United States Patent
Kasai

(10) Patent No.: US 7,692,837 B2
(45) Date of Patent: Apr. 6, 2010

(54) DEFLECTION DEVICE AND IMAGING APPARATUS

(75) Inventor: Shintaro Kasai, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 266 days.

(21) Appl. No.: 12/030,638

(22) Filed: Feb. 13, 2008

(65) Prior Publication Data

US 2008/0197286 A1 Aug. 21, 2008

(30) Foreign Application Priority Data

Feb. 16, 2007 (JP) ............................. 2007-035572

(51) Int. Cl.
*G02B 26/08* (2006.01)

(52) U.S. Cl. ............... 359/212.2; 359/209.1; 359/212.1; 359/223.1; 359/226.1; 359/18; 250/234

(58) Field of Classification Search ....................... None
See application file for complete search history.

(56) References Cited

U.S. PATENT DOCUMENTS

| 4,986,641 A * | 1/1991 | Braat ........................... 359/15 |
| 7,295,504 B2 * | 11/2007 | Kitazawa et al. ....... 369/112.03 |
| 2007/0148047 A1 | 6/2007 | Itsuji et al. |

FOREIGN PATENT DOCUMENTS

| JP | 60-68314 | 4/1985 |
| JP | 5-45600 | 2/1993 |
| JP | 2003-344791 | 12/2003 |

OTHER PUBLICATIONS

Juraj Darmo, et al., "Imaging with Terahertz Quantum Cascade Laser,"Optics Express, vol. 12, No. 9, pp. 1879-1884 (May 3, 2004).

* cited by examiner

*Primary Examiner*—James Phan
(74) *Attorney, Agent, or Firm*—Fitzpatrick, Cella, Harper & Scinto

(57) ABSTRACT

A deflection device includes a tabular object for transmitting or reflecting an electromagnetic wave, a drive unit for driving the tabular object so as to rotate or perform a translation motion, and an electromagnetic wave irradiation unit for irradiating the tabular object with an electromagnetic wave so that an irradiation area extending in a direction intersecting a direction of the rotation or translation motion of the tabular object is formed. The deflection device is characterized in that, in order to change a direction of transmission or reflection of an electromagnetic wave radiated on the irradiation area by the rotation or translation motion of the tabular object, a plurality of grooves extending in an in-plane direction of the tabular object is provided in a section of the tabular object along a longitudinal direction of the irradiation area, and the plurality of grooves is formed so that intervals of the plurality of grooves which passes through the irradiation area are changed by the rotation or translation motion of the tabular object.

8 Claims, 13 Drawing Sheets

DEFLECTION DEVICE AND IMAGING APPARATUS

BACKGROUND OF THE INVENTION

1. Field of the Invention

The present invention relates to a deflection device, which changes a propagation of an electromagnetic wave, and an apparatus, such as imaging apparatus using the same. In particular, the present invention relates to a deflection device which changes a propagation of an electromagnetic wave in a frequency domain of 30 GHz to 30 THz (in this specification, this is called a terahertz wave).

2. Description of the Related Art

Recently, engineering development using a terahertz wave is prosperous. In particular, applications to imaging are expected with taking advantage of transmission properties of the terahertz wave to various substances.

According to one proposal, organ imaging is performed using about 3.4 THz of terahertz wave (refer to OPTICS EXPRESS, Vol. 12, No. 9, pp. 1879, 2004 (Non-Patent Document 1)). In this proposal, an organ is placed in a focal position of a terahertz wave, and a terahertz wave image of the organ is obtained by moving the organ two-dimensionally.

In a terahertz wave area, development of an inexpensive and high-intensity light source and a highly sensitive detector is still insufficient. Therefore, it is hard to radiate electromagnetic wave on a whole object, to detect scattered waves, and to obtain an image, like in a visible and infrared area, or a radio wave area. In addition, a terahertz detector array is expensive and its sensitivity is also not sufficient. Hence, a method of converging and radiating a terahertz wave and detecting a reflected or transmitted wave from an object with a detector is performed widely.

However, since it is necessary in the method of Non-Patent Document 1 to move an imaging object two-dimensionally, it is hard to image a sample sensitive to vibration or acceleration. For example, when imaging a live creature, there is a possibility that the creature may move by moving a container into which the live creature is put.

In addition, the method of moving an imaging object needs a stage which can move a space which is large similarly to the object, so as to image a large object. On the other hand, in order to achieve imaging of a large object, it is also conceivable to adopt a system of deflecting a terahertz wave beam and making a focal position of a terahertz wave scanned on the object.

As beam deflection units, various units are proposed in areas of light and radio waves. What are known are a method of using a polygon mirror (refer to Japanese Patent Application Laid-Open No. H5-45600 (Patent Document 1)), a method of using an acousto-optic effect and an electro-optic effect, a method of using a diffraction grating (refer to Japanese Patent Application Laid-Open No. 2003-344791 (Patent Document 2)), and a method of using a holographic mirror (refer to Japanese Patent Application Laid-Open No. S60-68314 (Patent Document 3)).

SUMMARY OF THE INVENTION

In the case of using the above-mentioned polygon mirror for an imaging apparatus using a terahertz wave, size of the polygon mirror becomes as the following description, as an example.

Generally, when using a polygon mirror for an imaging apparatus, a method like the following is conceivable. That is, the method includes the steps of making electromagnetic wave be incident into the polygon mirror in a collimated beam, deflecting this collimated beam, and thereafter focusing the beam on an imaging object using a toric lens. Nevertheless, a wavelength of a terahertz wave is about 100 to 1000 times as large as a wavelength of light. Therefore, in order to obtain a collimated beam, unless a beam diameter is set to be about 10 mm or more, the beam will diverge because of a diffraction effect. Substantially, the beam diameter is set at about 40 mm in many cases. Since a large polygon mirror is necessary in order to deflect a beam with a diameter of not less than about 40 mm, a very large occupied volume is necessary.

As an example, suppose that a beam with a diameter of about 40 mm is deflected at an angle of 30° using a hexagonal polygon mirror. In order to deflect a beam at 30° lest an eclipse (this is that a part of beam protrudes from a mirror surface) of a beam by an angle of a polygon mirror should occur, it is necessary that length of one side is about 100 mm. That is, it is necessary that length of a diagonal line (equivalent to a diameter of a rotor at the time of rotating) is about 200 mm. In addition, since a beam diameter is about 40 mm, thickness of the polygon mirror needs to be not less than about 50 mm.

In addition, a material which deflects a terahertz wave by an acousto-optic effect or an electro-optic effect and obtains an effect equivalent to the polygon mirror is in a developmental stage. In particular, a terahertz wave damps greatly in process of transmitting a substance which generates an acousto-optic effect and an electro-optic effect.

Furthermore, in the proposal of Patent Document 2 using a diffraction grating for the purpose of scanning a light beam (laser beam) in an optical region, the diffraction grating is divided into a plurality of blocks, and respective blocks have different lattice constants. In this proposal, moving the diffraction grating perpendicularly to an optical axis in order to change a propagation of a light beam changes a lattice constant in a position where the light beam is incident into a diffraction grating. Since the diffraction directions are different when lattice constants are different, the propagation of a light beam changes and beam deflection is possible. However, in the method of the Patent Document 2, a change of the propagation of a beam is discontinuous and discrete.

In addition, in the proposal of Patent Document 3 using a holographic mirror, a disc is divided radially, a hologram which has a shape of a diffraction grating where an interval is different from those of others is arranged in each area, and a light beam is made to be incident into the disc. At this time, although the beam to be emitted is deflected by rotating the disc, this deflection is discrete. Hence, since a beam diameter of a terahertz wave is not less than about 10 mm, so as to deflect a terahertz wave beam by the method of Patent Document 3, a very large disc is necessary for smooth beam deflection.

The present invention is directed to a deflection device, comprising: a tabular object for transmitting or reflecting electromagnetic waves; a drive unit for driving the tabular object so as to rotate or perform a translation motion; and an electromagnetic wave irradiation unit for irradiating the tabular object with electromagnetic wave so that an irradiation area extending in a direction intersecting a direction of the rotation or translation motion of the tabular object is formed, wherein, in order to change a direction of transmission or reflection of electromagnetic wave radiated on the irradiation area by the rotation or translation motion of the tabular object, a plurality of grooves extending in an in-plane direction of the tabular object is provided in a section of the tabular object along a longitudinal direction of the irradiation area, and the plurality of grooves is formed so that intervals of the plurality of grooves which passes through the irradiation area are changed by the rotation or translation motion of the tabular object.

The tabular object can be rotatable by the drive unit around a rotation axis which passes a rotation center and intersects the plane of the tabular object perpendicularly, and the grooves are formed along a direction of the rotary action.

The tabular object can reciprocate linearly by the drive unit, and the grooves can be formed along a direction of the reciprocating motion.

The grooves can be formed so that intervals of the plurality of grooves in the irradiation area are arranged uniformly, or non-uniformly and regularly.

The tabular object can be constructed so as to perform not only a rotation or translation motion which the tabular object performs in an in-plane direction, but also a motion in a direction other than the in-plane direction by the drive unit or another drive unit, in order to deflect electromagnetic waves, radiated on the tabular object, two-dimensionally.

The plurality of grooves can be constructed so that intervals of the plurality of grooves which passes through the irradiation area are changed continuously by the rotation or translation motion of the tabular object.

The electromagnetic wave can be a terahertz wave.

The present invention is directed to an imaging apparatus, comprising: the deflection device according to claim 1; a detection unit; and a signal processing unit, wherein the detection unit detects an electromagnetic wave, which is reflected or transmitted from a measuring object, with moving an irradiation position of the electromagnetic wave radiated on the measuring object, using the deflection device, and the signal processing unit processes a detection signal from the detection unit to acquire an image of the measuring object.

Furthermore, another deflection device according to a second aspect of the present invention is a deflection device which changes a direction of transmission or reflection of an electromagnetic wave, which is incident there, by moving a tabular object, which transmits or reflects an electromagnetic wave, at least in a plane parallel to its plane, and has the following characteristic. This deflection device includes a tabular object in which at least one groove is formed, a drive unit which moves the tabular object, and an electromagnetic wave irradiation unit which makes an electromagnetic wave be incident into the tabular object. The at least one groove is formed in a tabular object so that a plurality of grooves may be arranged along a direction of forming an angle to the moving direction (typically, a rectangular direction). The electromagnetic wave irradiation unit makes an electromagnetic wave be incident in an area which extends in the direction of forming an angle to the moving direction of the tabular object (typically, a rectangular direction) and contains the plurality of grooves. Furthermore, the grooves are formed so that intervals of the plurality of adjacent grooves in an area in which the electromagnetic wave is made to be incident may change continuously in connection with a tabular object moving in the moving direction.

Moreover, in view of the problems, an imaging apparatus of the present invention includes the deflection device, a detection unit, and a signal processing unit. In this imaging apparatus, the detection unit detects an electromagnetic wave from the measuring object, with moving an irradiation position of the electromagnetic wave radiated on the measuring object, using the deflection device, and the signal processing unit processes a detection signal from the detection unit to acquire an image of the measuring object.

According to the present invention, it is possible to perform beam deflection continuously even for a terahertz wave with a comparatively long wavelength by a tabular object with comparatively small occupied volume.

Further features of the present invention will become apparent from the following description of exemplary embodiments with reference to the attached drawings.

DESCRIPTION OF THE EMBODIMENTS

Figure 1:
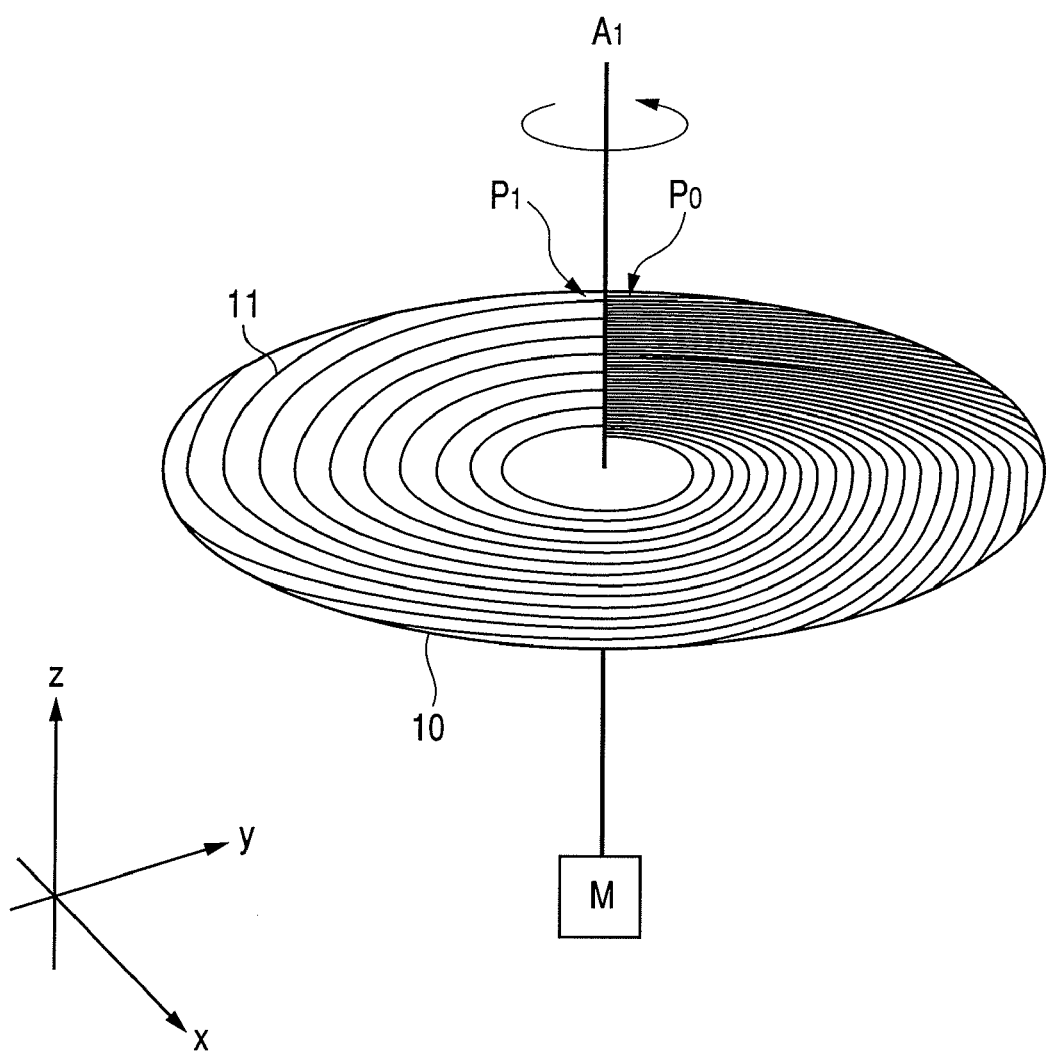
FIG. 1 is a perspective view illustrating a disc-shaped diffraction grating in a deflection device of an embodiment and Example 1 according to the present invention.

Embodiments of a deflection device according to the present invention will be described with referring to drawings.

The deflection device is constructed of including a tabular object, a drive unit, and an electromagnetic wave irradiation unit.

This tabular object (a member 11 in FIG. 1 and a member 10 in FIG. 2) is a member for transmitting or reflecting an electromagnetic wave.

The drive unit is a unit for driving the tabular object so as to rotate or perform a translation motion.

The electromagnetic wave irradiation unit is a unit for irradiating the tabular object with an electromagnetic wave so that an irradiation area (reference numeral 20 in FIG. 2) extending in a direction intersecting a direction of the rotation or translation motion of the tabular object is formed.

In order to change a direction of transmission or reflection of an electromagnetic wave radiated on the irradiation area by the rotation or translation motion of the tabular object, grooves are formed in the object.

Specifically, a plurality of grooves extending in an in-plane direction of the tabular object is provided in a section of the tabular object along a longitudinal direction (reference numeral 299 in FIG. 2) of the irradiation area. Here, the section means a face, which is perpendicular to the tabular object, along a longitudinal direction.

The plurality of grooves is formed so that intervals of the plurality of grooves which passes through the irradiation area are changed by the rotation or translation motion of the tabular object.

Since intervals of the plurality of grooves in the irradiation area 20 can change continuously or intermittently by adopting such construction, it is possible to scan a deflection direction irradiated. In addition, the grooves extending in the in-plane direction of the tabular object may be grooves each of which is continuous, or concavities each of which is slender or separated dots.

The present invention will be described below in detail.

In the disc-shaped diffraction grating 10 of the embodiment shown in FIG. 1, the plurality of grooves 11 is trenched in a direction which approximately coincides with a circumferential direction of a disc which is a tabular object. A slender diffraction grating extending radially from a center is formed in each minute central angle portion over 360° around the center. This diffraction grating is equipped with structure of an ordinary diffraction grating specified with a lattice constant. Furthermore, a period of the grooves (an interval of adjacent grooves which is a lattice constant) is made to transfer continuously from a period $P_0$ to a period $P_1$ gradually as illustrated in FIG. 1. In this embodiment, the period of grooves is substantially constant in each slender diffraction grating.

In other words, in this embodiment, in order to deflect a terahertz wave in comparatively small occupied volume, the following construction is adopted. That is, one or more grooves 11 are formed in the tabular object 10 which is made of a material which transmits or reflects an electromagnetic wave, and each of the grooves 11 has a finite radius of curvature in a direction perpendicular to a section of the grooves 11. When the groove is one, it is spirally formed around a center. In addition, the tabular object 10 has a rotation center at one arbitrary point, and has a rotation axis $A_1$ which passes through this rotation center and intersects perpendicularity to a plane of the tabular object 10. By rotating this axis by a motor M or the like which is a drive unit, the tabular object 10 is rotated within a plane parallel to the plane. In addition, arbitrary half-lines whose one ends are the rotation center, and which are parallel to the face of the tabular object 10 intersect multiple times with the grooves 11, and intervals of intersections of these straight lines and grooves 11 are arranged so as to be uniform, or non-uniform and regulative (approximately uniform in the example in FIG. 1). A terahertz wave is radiated by the electromagnetic wave irradiation unit in an area along this half-line. Furthermore, the intervals of the adjacent grooves 11 change continuously along a rotation direction of the rotation axis $A_1$. Hence, when the tabular object 10 is rotated around the rotation axis, the intervals of the intersections of the half-lines and grooves 11 change continuously. In consequence, the terahertz wave radiated on the area receives an operation of the slender diffraction grating with the lattice constant, which changes continuously, to be deflected as mentioned later.

The direction perpendicular to a section of a groove which is mentioned above is a direction where the groove extends. In addition, that a direction perpendicular to a section of a groove has a finite radius of curvature that is described above means that the groove does not extend straightly but extends curvilinearly. That is, it is not a meaning of that a bottom face of a groove is roundish. Nevertheless, it does not exclude that the bottom face of a groove is roundish.

In the construction, a terahertz wave is radiated on a line segment (the half-line) which connects the rotation center of the tabular object 10 to one arbitrary point on its edge, and the tabular object 10 is rotated with an irradiation position of the terahertz wave being fixed. Thereby, the radiated terahertz wave is diffracted by the groove 11 formed on the tabular object 10, and is reflected or transmitted in a direction corresponding to an interval of the grooves 11. In this way, it is possible to change continuously the traveling direction of a reflected or transmitted terahertz wave which is diffracted, by rotating the tabular object 10. That is, it is possible to deflect a terahertz wave beam.

Figure 2:
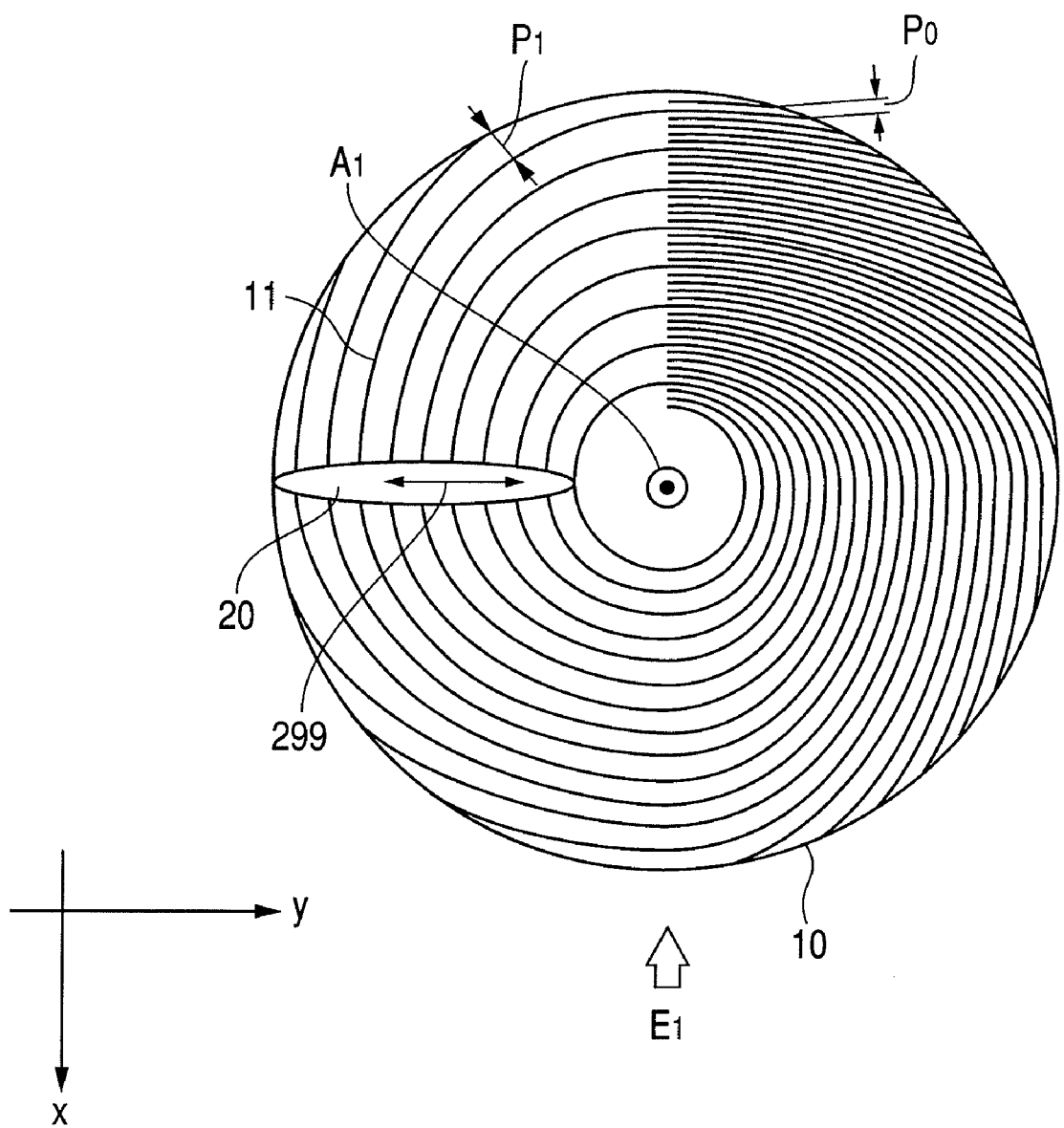
FIG. 2 is a top view of the disc-shaped diffraction grating in FIG. 1 with viewing from a direction of a rotation axis $A_1$.

FIG. 2 is a top view of the disc-shaped diffraction grating 10 with viewing from a direction of the rotation axis $A_1$, and is a drawing with viewing from a z direction of coordinates illustrated in FIG. 1. In the deflection device of this embodiment, a terahertz wave is shaped into a parallel ray with a linear or slender and elliptic sectional beam profile as illustrated by reference numeral 20 in FIG. 2 using a cylindrical lens or the like, and is radiated. In this way, the beam spot 20 extending radially is formed on the disc-shaped diffraction grating 10. As mentioned above, on the beam spot 20, it is possible to regard that the intervals of the grooves 11 of the slender diffraction grating are approximately constant. Nevertheless, it is also sufficient to make a terahertz wave condensed on the disc-shaped diffraction grating 10 so as to have a sectional beam profile. That is, it may not be a parallel ray, but may be a convergent ray. As a unit to generate a terahertz wave, a Backward Wave Oscillator (BWO), a terahertz parametric oscillator, or the like can be used.

Figure 3:
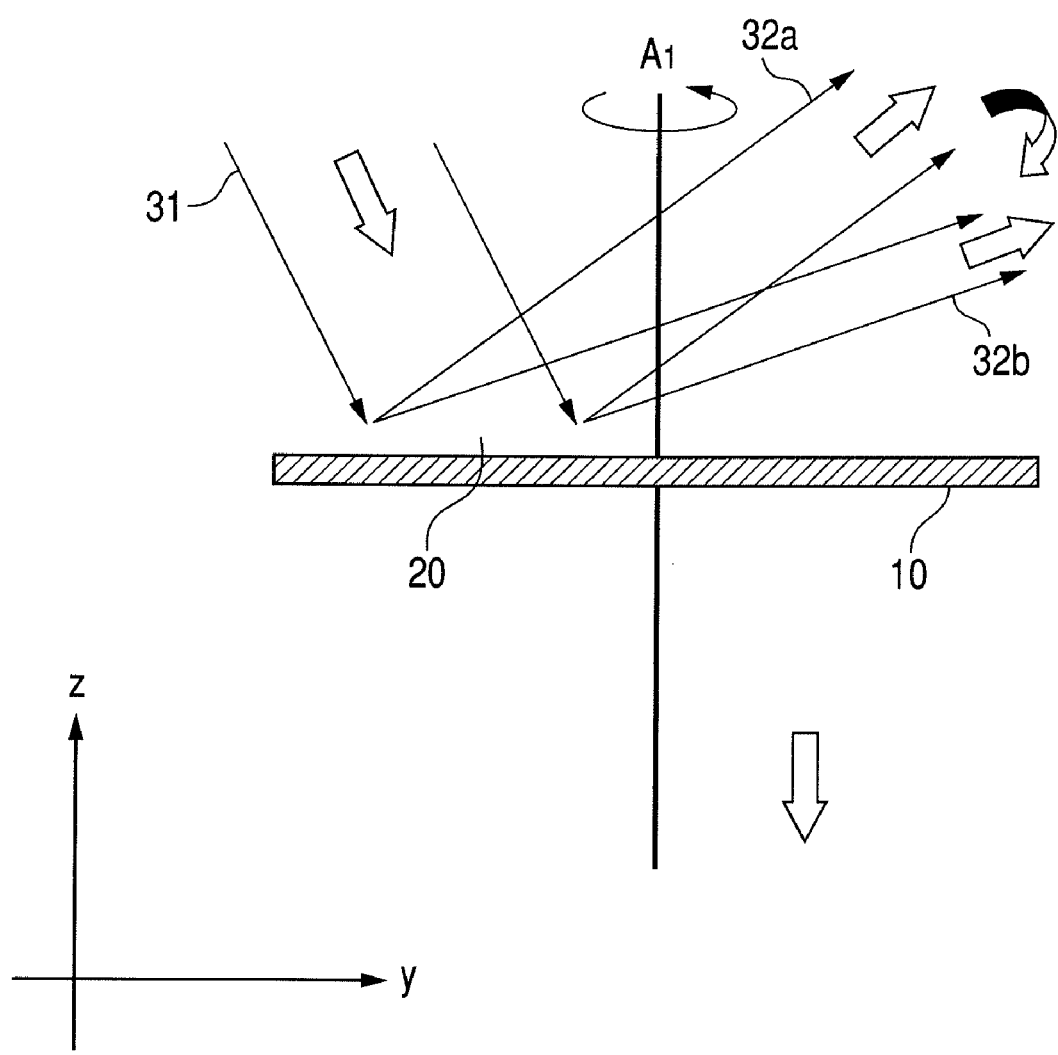
FIG. 3 is a schematic diagram illustrating an aspect that electromagnetic wave deflection is executed using the disc-shaped diffraction grating in FIG. 1.
Figure 4A:
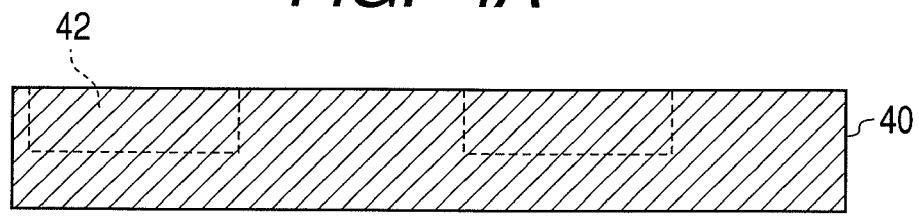
FIGS. 4A, 4B, 4C and 4D are schematic sectional views illustrating examples of processes of forming grooves in the disc-shaped diffraction grating according to the present invention.
Figure 4B:
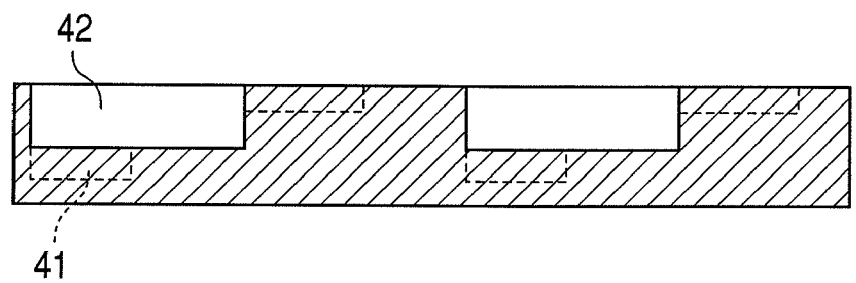
Figure 4C:
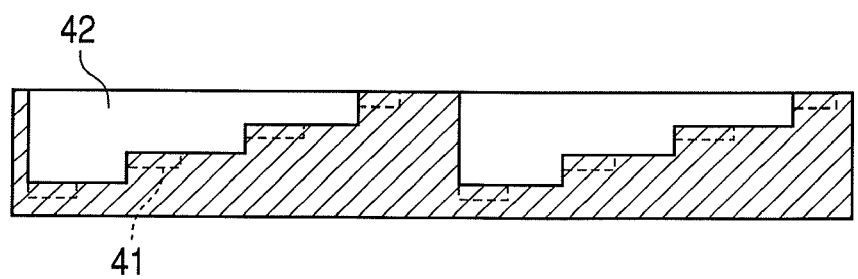
Figure 4D:
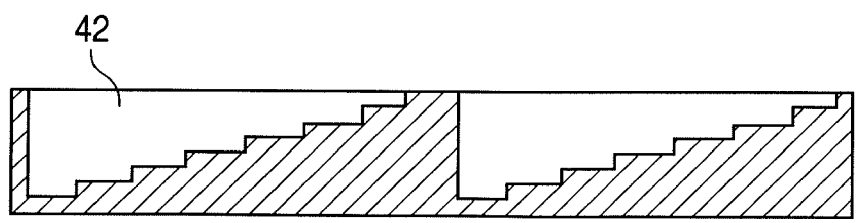

FIG. 3 is a sectional view of the disc-shaped diffraction grating 10 with viewing from a direction of E1 in FIG. 2, and is a sectional view with viewing from a section including the rotation axis $A_1$ (it is a yz in-plane section). An incidence terahertz wave 31 is diffracted within the yz plane to an angle corresponding to a lattice constant of the slender diffraction grating on the beam spot 20. Here, since the lattice constant on the beam spot 20 changes as mentioned above when the disc-shaped diffraction grating 10 is rotated around the rotation axis $A_1$, a diffraction angle changes and, therefore, the terahertz wave beam 31 is deflected within the yz plane. FIG. 3 illustrates an aspect that a propagation of the diffracted terahertz wave changes from a beam 32a to a beam 32b.

By the way, the above-mentioned embodiment can be modified variously within a range of the following basic construction of a deflection device of the present invention. In the basic construction, grooves are formed so that a plurality of grooves may be located in a direction rectangular to a moving direction of a tabular object, an electromagnetic wave is incident into an area which extends in a direction which forms an angle to the moving direction, and contains a plurality of grooves, and the grooves are formed so that intervals of the adjacent grooves in this area may change continuously with a motion. Typically, the direction which forms an angle to this moving direction is a direction rectangular to the moving direction, as mentioned above. Within the range of this basic construction, as described above, the tabular object is not limited to a disc-shaped diffraction grating, which is constructed of slender diffraction gratings ranging, but may be a tabular object which is rectangular and reciprocates linearly. The number of grooves is not limited to two or more, but a form that one groove is spirally formed is possible as mentioned above. In each of the slender diffraction gratings also, the intervals of grooves may not be uniform. By a principle of Fresnel zone plate production, the intervals of grooves may be non-uniform and may change regularly.

In addition, the tabular object does not need to be one sheet of flat plate, but may be an object that a groove is formed in the object constructed of two or more sheets being stacked. The groove is not limited to a groove where a space trenched remains as it is, but may be a groove where a space is filled up with an adequate material. In short, in an area like the slender diffraction grating on which an electromagnetic wave is radiated, it is sufficient that a groove is formed so that a dielectric constant distribution which exerts a certain diffraction operation to an electromagnetic wave, and leads to beam deflection may be established. Furthermore, a target electromagnetic wave is a terahertz wave, an advantageous effect of which is remarkable, typically as mentioned above, but even electromagnetic waves in other frequencies can be used.

Furthermore, since characteristics of the grooves and the like are exaggeratedly drawn in the drawings referred to above, the drawings not always reflect realistic size faithfully. The embodiment which mixed the numerical example of the realistic size is described hereinafter.

EXAMPLES

Example 1

A first example of the present invention will be described. In this example, a silicon substrate with 4 inches (about 100 mm) of diameter is used as a tabular disc of the disc-shaped diffraction grating 10 illustrated in FIG. 1. On the silicon substrate, a plurality of approximately circular grooves 11 as shown in FIG. 1 is formed. That is, the plurality of grooves 11 is formed along an approximate direction of rotation of the disc. The plurality of approximately round grooves 11 formed on the silicon substrate is about 0.16 mm (about 6.1 lines per mm) at its narrowest interval, and is about 0.63 mm (about 1.6 lines per mm) at its widest interval. Groove intervals or grid intervals change toward a circumference (the direction of the rotation) continuously, as illustrated in FIG. 1 or 2. Hence, the groove 11 has a form that a lattice constant of a slender diffraction grating which extends in a radial direction and is provided around a center of the disc changes continuously.

Figure 5:
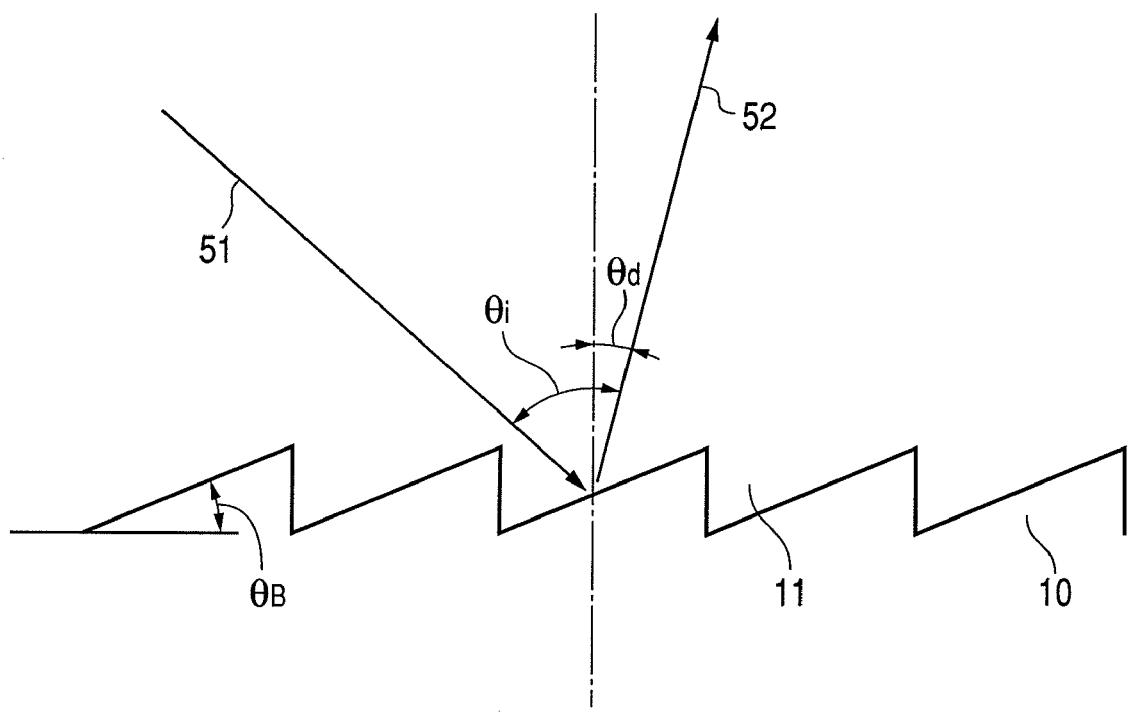
FIG. 5 is a sectional view illustrating an operation of a groove formed in the disc-shaped diffraction grating.

The grooves 11 can be formed on a silicon substrate using photolithography and reactive ion etching, and the like. As illustrated in FIGS. 4A to 4D illustrating forming steps, it is possible to form step-wise grooves by repeating two or more times the photolithography and reactive ion etching. Here, reference numeral 40 denotes a silicon substrate, and an area surrounded by a dotted line 41 is removed by a method such as reactive ion etching. Thereby, a cavity 42 is formed. It is better to make an angle of the step-wise groove, formed in this way, become a blaze angle $\theta_B$, which emphasizes a specific order of diffracted wave, in each slender diffraction grating as illustrated in FIG. 5.

In the figures of the groove intervals cited above, it is possible to diffract 3 THz of incident light 51, which is incident at an incident angle $\theta_I$ 60°, to a primary diffracted wave 52 at a diffraction angle $\theta_d$ of 15° ($\theta_B$ 22.5°) to 45° ($\theta_B$ 7.5°). It is as illustrated in FIG. 5 which angles the incident angle, diffraction angle, and blaze angle denote respectively. Hence, in each slender diffraction grating with a predetermined groove interval, it is good to make an angle of the groove become the blaze angle which emphasizes the primary diffracted wave. For the purpose, what necessary is just to change the blaze angle of the groove from 22.5° to 7.5° continuously in a slender diffraction grating with the narrowest groove interval to a slender diffraction grating with the widest groove interval.

When a desired diffraction grating pattern can be formed on a silicon substrate by photo lithography and reactive ion etching, or the like, a metal thin film (for example, gold) may be attached on its surface by a method, such as vapor deposition, in order to enhance reflectance of a terahertz wave.

When using the disc-shaped diffraction grating 10 cited above, it is possible to perform beam deflection of a terahertz wave whose beam diameter is about 40 mm in a range of an angle of 30°. Size of the disc-shaped diffraction grating 10 at this time is about 100 mm in diameter, about 0.5 mm in thickness, and about 3900 mm$^3$ in volume. On the other hand, the following size is necessary when the right hexagonal polygon mirror which has comparable performance is considered. That is, it is necessary that length of one side (length of a diagonal line (equivalent to a diameter of a rotor at the time of rotating) is about 200 mm) is 100 mm, and thickness is 50 mm. For this reason, volume becomes about $1.3 \times 10^6$ mm$^3$, and it turns out that a volume ratio of the disc-shaped diffraction grating of this example to a conventional polygon mirror becomes about 1/1000. Thereby, in this example, miniaturization of a device is possible. In addition, since this is small, weight saving is expectable, and thereby, energy saving for driving a disc-shaped diffraction grating is also possible.

Example 2

Figure 6:
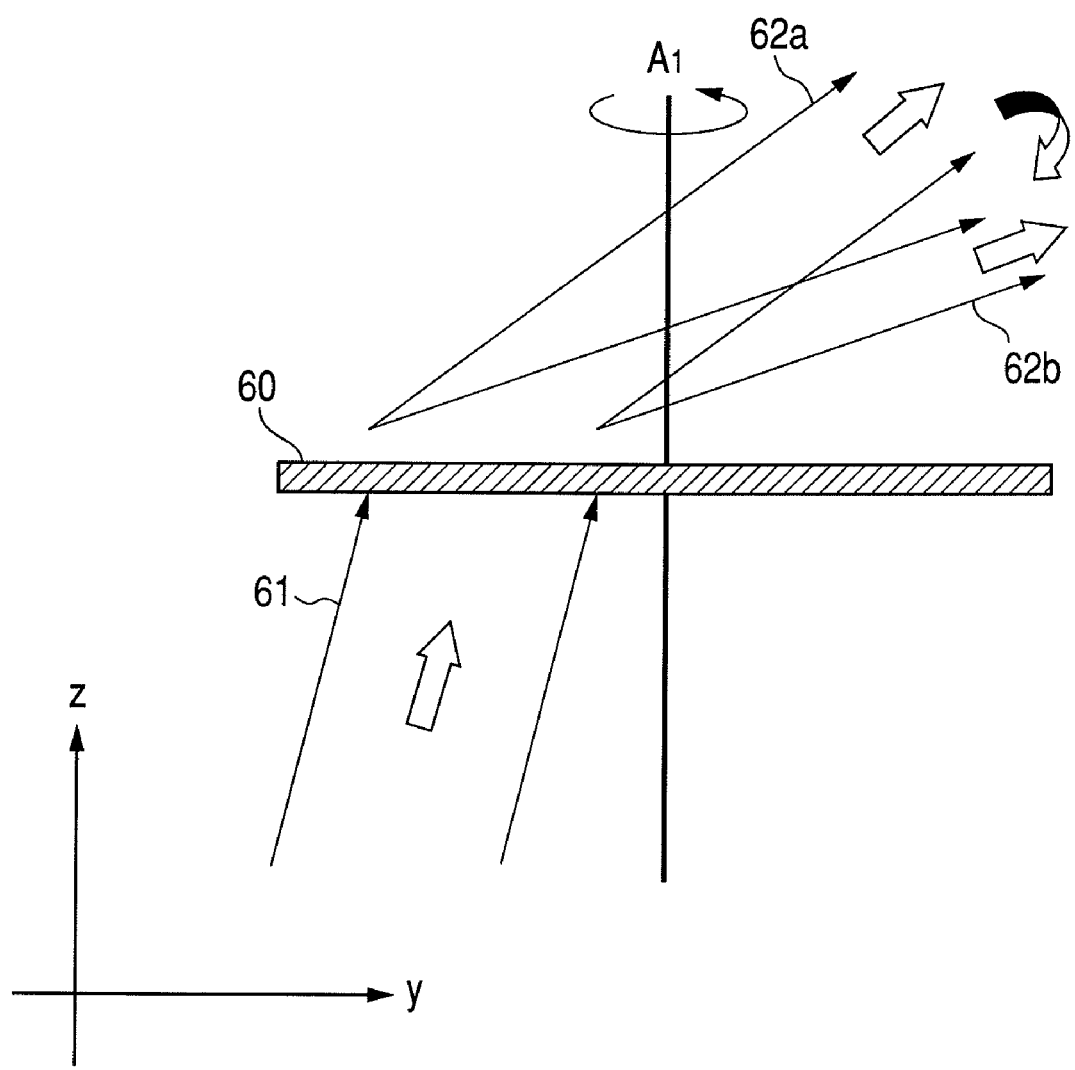
FIG. 6 is a schematic diagram illustrating a transmissive-type disc-shaped diffraction grating in a deflection device of Example 2 according to the present invention.

Example 2 of the present invention will be described with referring to FIG. 6. A disc-shaped diffraction grating 60 illustrated in FIG. 6 is constructed by forming grooves in intervals, as described in Example 1, in a tabular disc which is made of a material whose permeability to a terahertz wave is high, such as high resistivity silicon or polyethylene. Similarly to Example 1, an elongation direction of the grooves meets an approximately circumferential direction, and groove intervals are different in each slender diffraction grating, as illustrated in FIGS. 1 and 2. Specifically, the groove interval changes continuously along a circumferential direction. Nevertheless, in the each slender diffraction grating extending radially, the groove interval is constant similarly to Example 1. Although it is assumed that the grooves are formed in a top face of the disc-shaped diffraction grating 60 in FIG. 6, they may be formed in a back face or both faces.

In this embodiment, a terahertz wave 61 is made to be incident into one face (for example, a back face) of the disc-shaped diffraction grating 60 in a beam spot as denoted by reference numeral 20 in FIG. 2. The terahertz wave which transmits the each slender diffraction grating of the disc-shaped diffraction grating 60 is diffracted at a diffraction angle corresponding to a groove interval of an incident position, and propagates in a direction different from an incident direction like beams denoted by reference numerals 62a and 62b. Since it is possible to change continuously a direction of diffraction from the beam 62a to the beam 62b by rotating the disc-shaped diffraction grating 60 around the central axis $A_1$, it is possible to achieve beam deflection. This beam deflection returns to the original position in an instant every rotation end, and is repeated. This is also the same as in Example 1.

This example uses transmission type layout, and hence, has an advantage that handling of a terahertz wave beam becomes easy. That is, since beams of an incidence terahertz wave and a reflected (diffracted) terahertz wave approach in a reflection type, a device for separating these (for example, a device of arranging adequately optical systems, such as a mirror, to lead a diffracted wave in a direction of an object) is necessary. On the other hand, in this example, a special device for separation of an incidence terahertz wave and a transmitted (diffracted) terahertz wave is unnecessary, and hence, the separation is easy. Other respects are the same as those in Example 1.

Example 3

Figure 7:
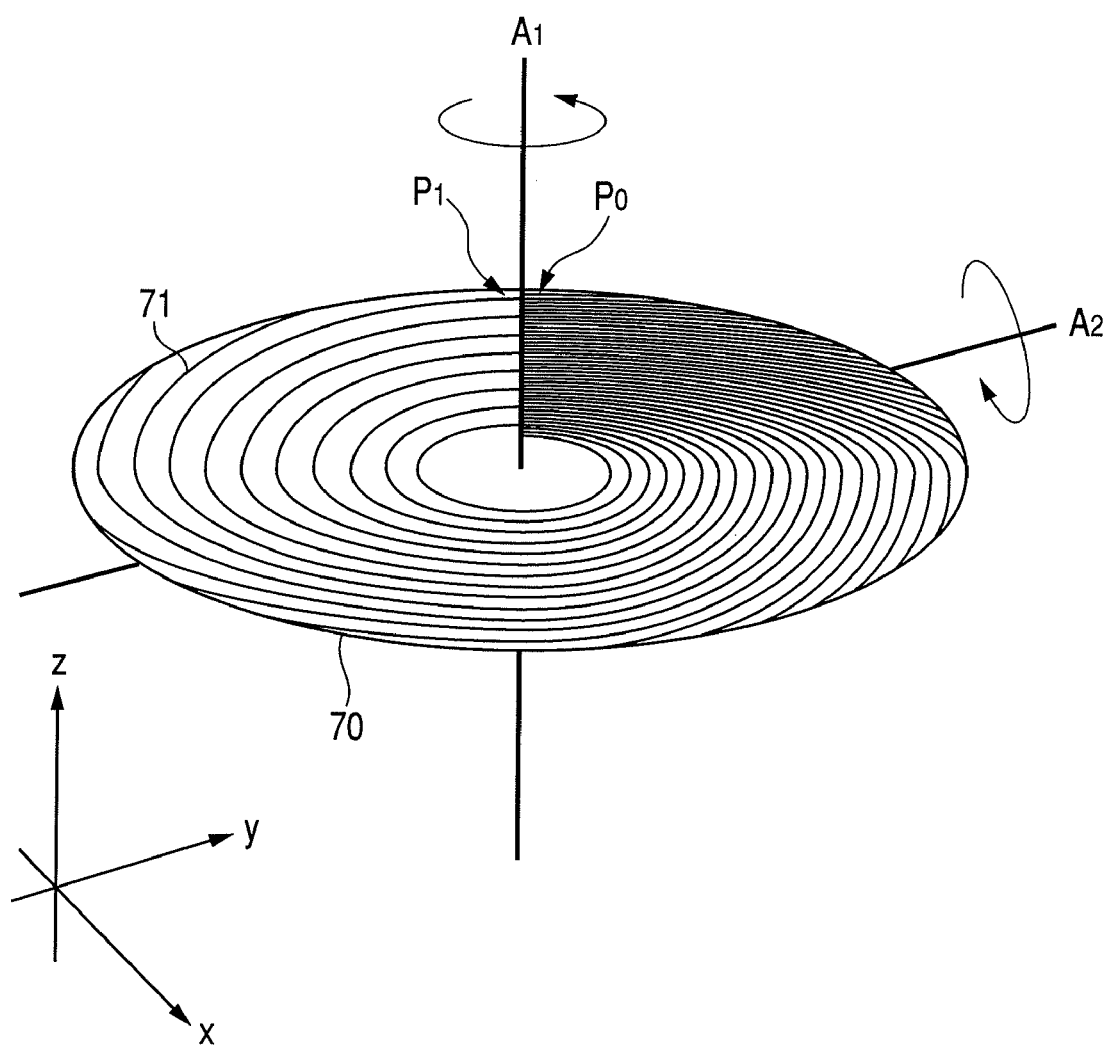
FIG. 7 is a perspective view illustrating a disc-shaped diffraction grating with two rotation axes in a deflection device of Example 3 according to the present invention.

Example 3 of the present invention will be described using FIGS. 7 to 10. Similarly to Example 1, a disc-shaped diffraction grating 70 illustrated in FIG. 7 is a tabular object that grooves 71 are formed in a silicon substrate or the like. A plurality of grooves 71 is trenched in a direction corresponding approximately to a circumferential direction of a disc, and the each slender diffraction grating extending radially is formed around a center. Although intervals of the adjacent grooves 71 along a radial direction are approximately constant in the each slender diffraction grating extending radially, these groove intervals change along a circumferential direction. In this way, a period of the grooves 71 (lattice constant) is made to transfer continuously from the period $P_0$ to the period $P_1$ gradually as illustrated in FIG. 7.

In this example, the disc-shaped diffraction grating 70 is perpendicular to a diffraction grating face, and can rotate around the axis $A_1$, passing through a center of an approximate circle which the diffraction grating groove 71 forms, as a rotation axis. In addition, the diffraction grating intersects the rotation axis $A_1$ perpendicularly and can rotate also around another axis $A_2$ on the diffraction grating face as a rotation axis. As a mechanism of achieving such rotation, a supporting mechanism used in a gyroscope can be used, for example. That is, an inside housing supports the disc-shaped diffraction grating 70 rotatably around the axis $A_1$, and an outside fixed frame supports this inside housing rotatably around an axis corresponding to the another axis $A_2$. A rotational driving force may be given to each rotation axis by a motor provided in each housing, for example.

Figure 8:
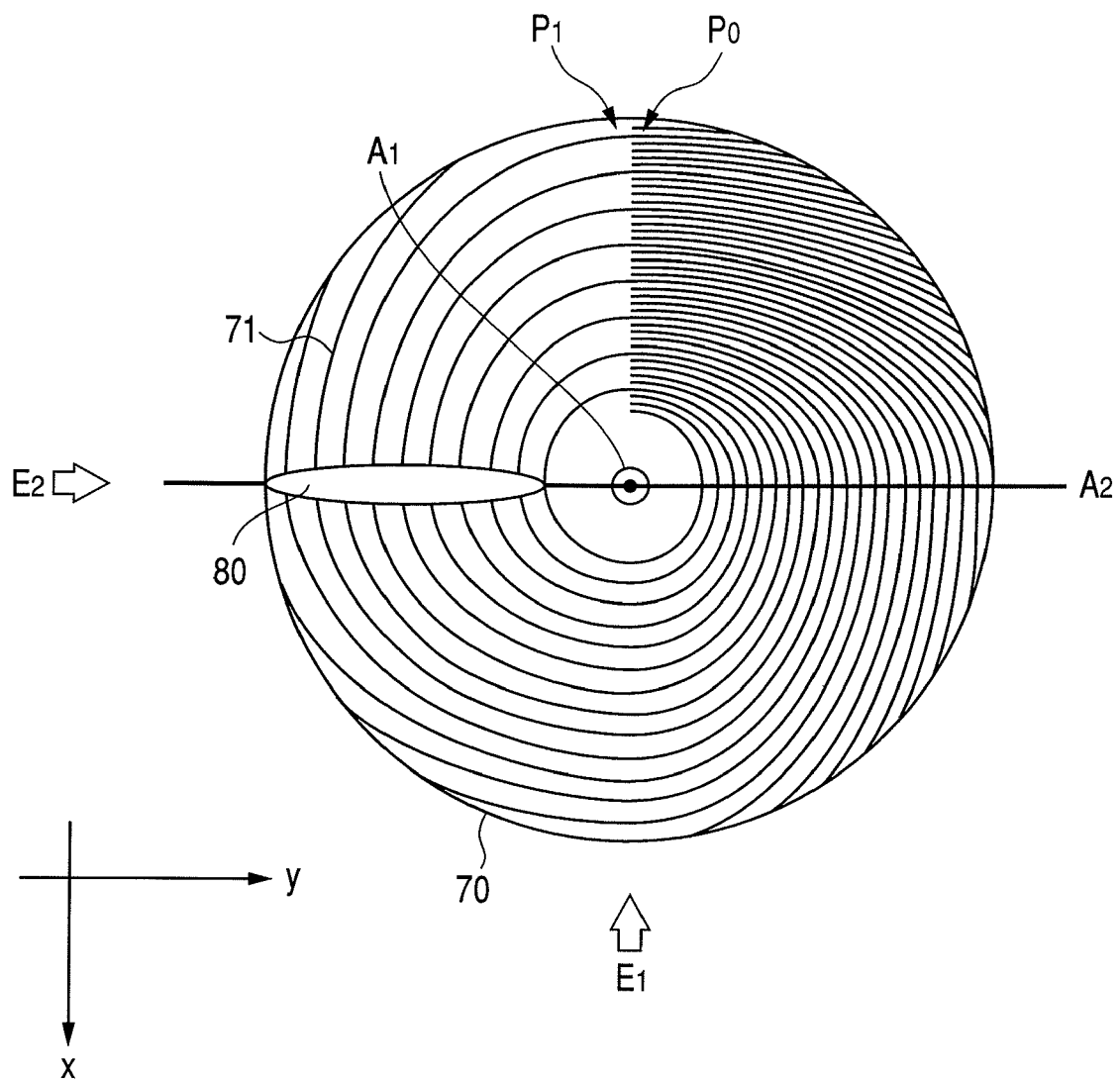
FIG. 8 is a top view of the disc-shaped diffraction grating in FIG. 7 with viewing from the direction of the rotation axis $A_1$.

FIG. 8 is a top view of the disc-shaped diffraction grating 70 with viewing from a direction of the rotation axis $A_1$ (this is a drawing corresponding to FIG. 2). A terahertz wave from a terahertz wave generation unit is shaped into a parallel ray with a linear (or slenderly elliptic) sectional beam profile as denoted by reference numeral 80 in FIG. 8, using a cylindrical lens or the like. Then, this is radiated on the disc-shaped diffraction grating 70, and a beam spot 80 is formed. On the beam spot 80 extending in a radial direction, it is possible to regard that diffraction grating intervals are approximately constant. In this example, the beam spot 80 is radiated as it is on each slender diffraction grating which arrives on the rotation axis $A_2$.

Figure 9:
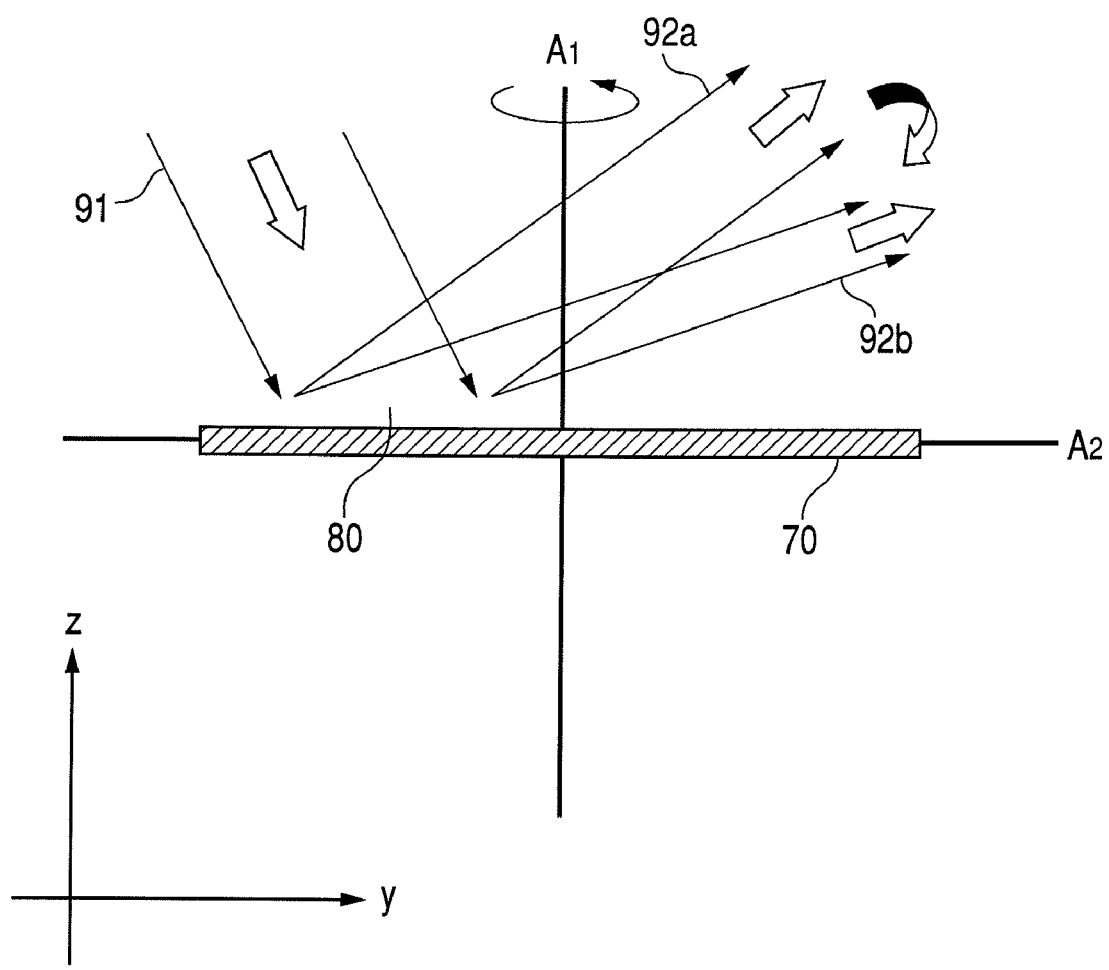
FIG. 9 is a schematic diagram illustrating an aspect that electromagnetic wave deflection is executed using the disc-shaped diffraction grating in FIG. 7.

FIG. 9 is a sectional view of the disc-shaped diffraction grating 70 with viewing from a direction of $E_1$ in FIG. 8, and is a sectional view with viewing from a section including the rotation axis $A_2$ (it is a yz in-plane section). An incidence terahertz wave 91 is diffracted within the yz plane toward an angle corresponding to a lattice constant of the each slender diffraction grating arriving at a position of the beam spot 80. FIG. 9 illustrates an aspect that a propagation of the diffracted terahertz wave changes from a beam 92a to a beam 92b.

Figure 10:
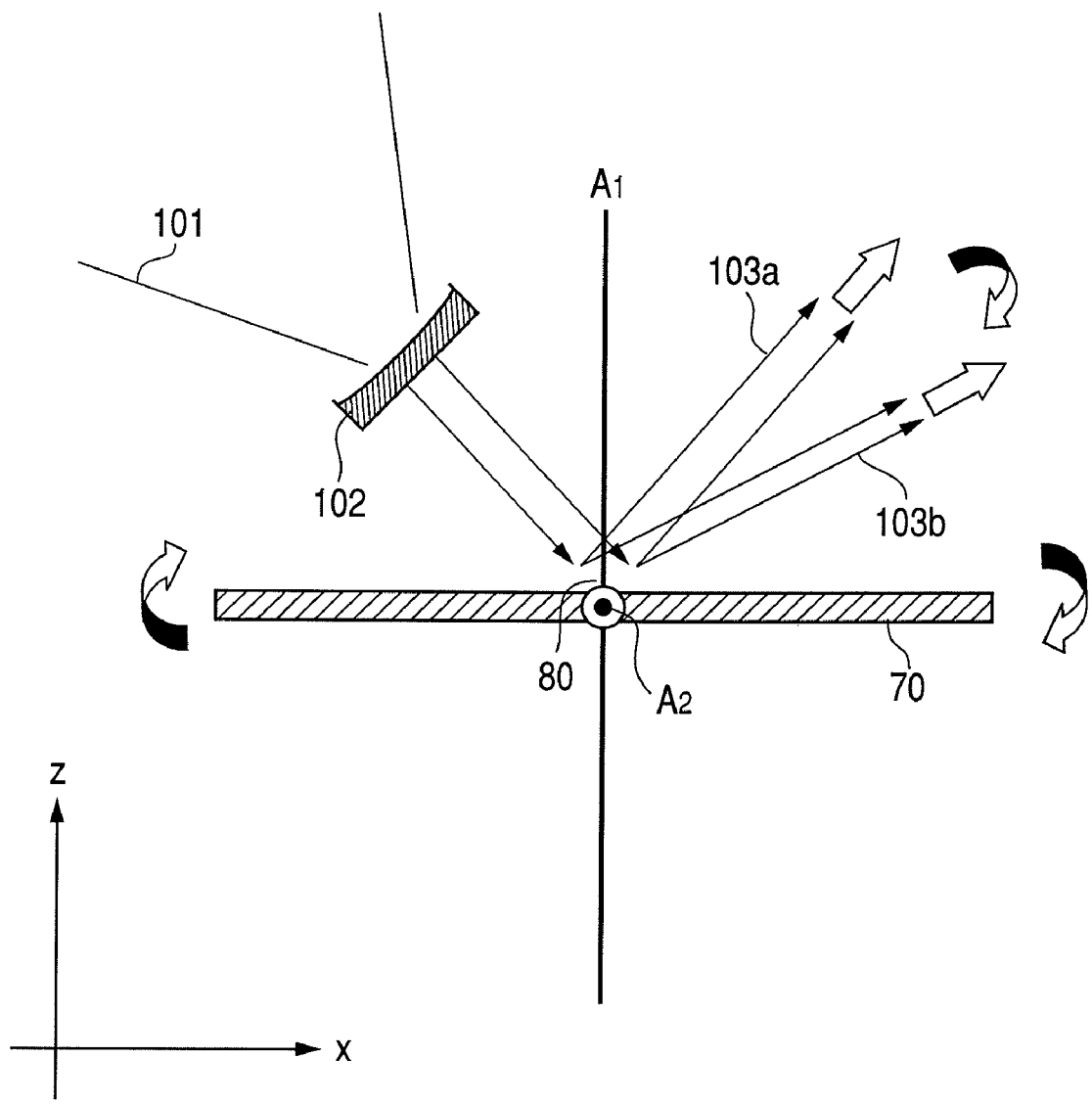
FIG. 10 is a schematic diagram illustrating an aspect that electromagnetic wave deflection is executed using a second rotation axis of the disc-shaped diffraction grating in FIG. 7.

FIG. 10 is a sectional view of the disc-shaped diffraction grating 70 with viewing from a direction of $E_2$ in FIG. 8, and is a sectional view with viewing from a plane vertical to the rotation axis $A_2$ (it is an xz in-plane section). An incidence terahertz wave 101 passes through a cylindrical lens 102 to be shaped into a parallel ray with a linear or slenderly elliptic sectional beam profile, and is condensed on the each slender diffraction grating on the rotation axis $A_2$ as a beam spot 80.

Here, the incidence terahertz wave 101 is reflected by the disc-shaped diffraction grating 70. Since a direction of viewing the section in FIG. 10 is parallel to a direction where the each slender diffraction grating extends, a diffraction operation does not occur in the xz plane, and hence, a reflecting direction of the incidence terahertz wave is uniquely decided by a law of reflection.

When rotating the disc-shaped diffraction grating 70 around the rotation axis $A_2$ like arrows illustrated in the right and left of the diffraction grating 70 in FIG. 10, the reflected terahertz wave 103a changes into a reflected terahertz wave 103b. Therefore, a terahertz wave beam is deflected within the xz plane.

When rotating the disc-shaped diffraction grating 70 around the rotation axes $A_1$ and $A_2$ according to the aspects described above, it is possible to deflect a terahertz wave beam two-dimensionally in two directions of the yz in-plane direction and xz in-plane direction.

In addition, the incidence terahertz wave 91 and the incidence terahertz wave 101 are completely the same, and only the observation viewpoints are different. Furthermore, although a lens 102 in FIG. 10 is not drawn in FIG. 9, this is because the lens 102 does not have a function optically within the yz plane in FIG. 9 and it is omitted.

According to construction of this example, it is possible to deflect two-dimensionally a terahertz wave beam radiated on the each slender diffraction grating which arrives on the rotation axis $A_2$. Other respects are the same as those in Example 1.

Example 4

Figure 11:
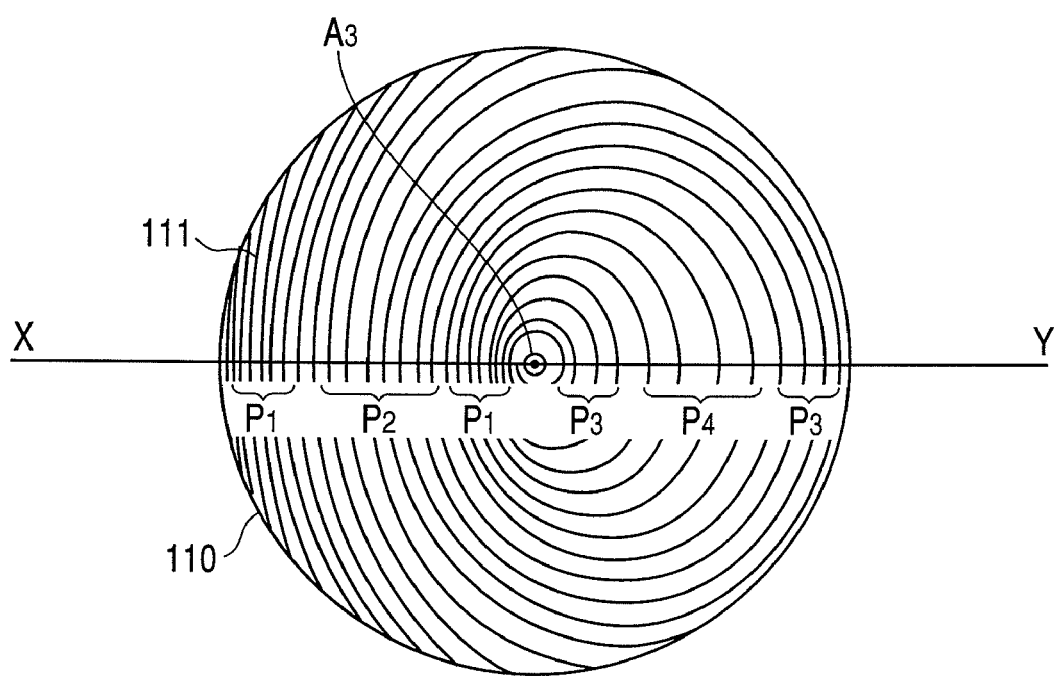
FIG. 11 is a top view of a disc-shaped cylindrical lens with an electromagnetic wave condensing function in a deflection device of Example 4 according to the present invention with viewing from a direction of a rotation axis $A_3$.

Example 4 of the present invention will be described with referring to FIG. 11. Also in this example, grooves 111 are formed in a disc (disc-shaped cylindrical lens) 110, made of high resistivity silicon or the like, by a methods such as photo lithography and reactive ion etching. In this example, on an XY line passing through a center of the disc 110, intervals of the grooves 111 near the center and a circumference are narrow in an X side from a center, and intervals of the grooves 111 in portions other than them are wider than those near the center and circumference. In addition, similarly in a y side from the center, intervals of the grooves 111 are narrow near the center and the circumference, and intervals of the grooves 111 are wide in portions other than them.

For example, the interval of the grooves 111 changes non-uniformly and regularly according to a formula expressing an interval of an orbicular zone of a Fresnel zone plate, or the like. As schematically illustrated in FIG. 11, for example, in an X side from a center, an area described as $P_1$ has narrow intervals of the grooves 111, and an area described as $P_2$ has wide intervals of the grooves 11. Nevertheless, the intervals of the grooves 111 change continuously, but do not change discretely in $P_1$ and $P_2$. In addition, also in a Y side from the center, intervals of the grooves 111 in an area described as $P_3$ are narrower than intervals in an area described as $P_4$. Furthermore, the intervals of the grooves 111 are different in the X side from the center and the Y side from the center, and for example, the intervals of the grooves 111 in $P_1$ are narrower than those in $P_3$, and the intervals of the grooves 111 in $P_2$ are narrower than those in $P_4$. That is, the intervals of a plurality of grooves 111 change continuously along an approximately circumferential direction so that such a form may be achieved. In consequence, in this example, when the disc 110 is rotated around a rotation axis $A_3$, each slender portion which arrives in a slender area on which a terahertz wave beam is radiated plays the function of a cylindrical lens.

Operation of the above constitution will be described. Similarly to Example 2, a terahertz wave which is condensed in a line or an elliptic is made to incident into one face of the disc 110. For example, the terahertz wave is radiated on an area radially extending from the center to the X side. The transmitting terahertz wave is diffracted by the grooves of each slender portion of the disc 110 which arrives in an irradiation portion. At this time, when groove intervals of each slender portion radially change adequately and continuously, the diffracted terahertz wave is condense or diverged. That is, the each slender portion which constructs the disc 110 has a lens action by the same principle as a Fresnel lens zone plate. Nevertheless, only one direction has a lens action, which is the same operation as a cylindrical lens.

Here, since the groove intervals of each slender portion by which a terahertz wave is affected change when the disc 110 which is a disc-shaped cylindrical lens is rotated around the central axis $A_3$, an extent of condensing or divergence of the diffracted terahertz wave changes. That is, a focal length of each slender lengthy portion of the disc 110 with a lens action changes. Thus, the disc 110 can be operated as a lens with variable focal length to a terahertz wave. In this example, when the disc 110 is rotated around two axes like Example 3, the focal length can be changed with the diffracted terahertz wave being deflected two-dimensionally.

Example 5

Figure 12:
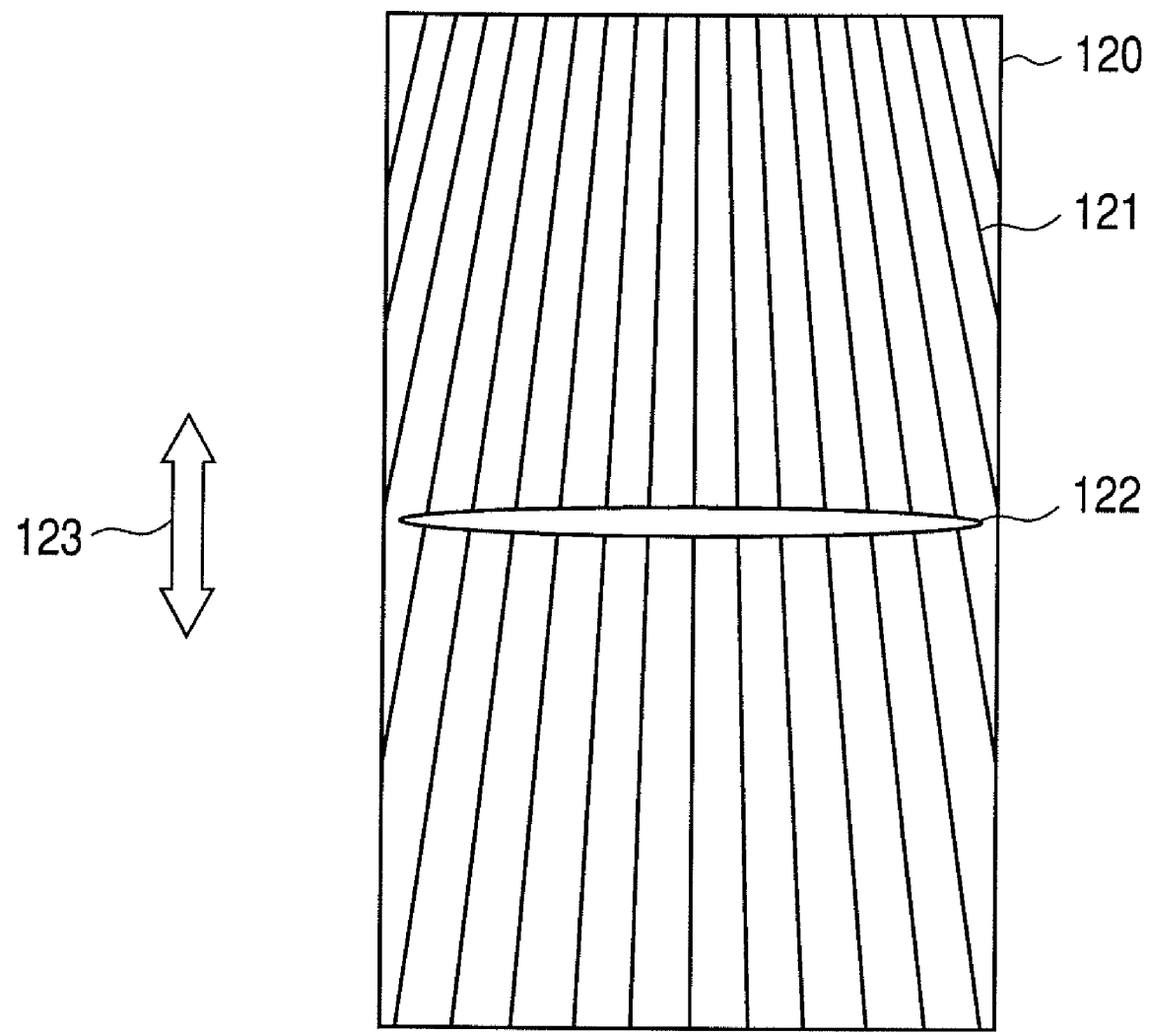
FIG. 12 is a top view illustrating a diffraction grating, performing a reciprocating motion, in a deflection device of Example 5 according to the present invention.

Example 5 of the present invention will be described with referring to FIG. 12. In this example, in a rectangular flat plate (reciprocating motion diffraction grating) 120 which is constructed of a silicon substrate and the like, a plurality of grooves 121 is formed. Intervals of the grooves 121 are different in positions (portions extending in a direction approximately orthogonal to a moving direction 123) along the approximate moving direction. The flat plate 120 can reciprocate linearly in the moving direction shown in FIG. 12. A normal unit using a motor or the like can be used also as a drive unit of this reciprocating motion.

An operation of this embodiment will be described. A terahertz wave is radiated on a part illustrated by reference numeral 122 (a slender portion extending in a direction approximately orthogonal to the moving direction, and here, intervals of the grooves 121 are approximately uniform), and the flat plate 120 is made to reciprocate. This moves an irradiation position of the terahertz wave relatively on the flat plate 120, and the intervals of the grooves 121 of each slender diffraction grating which the terahertz wave is affected change. This is equivalent to a change of a lattice constant of the diffraction grating, and hence, a direction of a diffraction angle of the terahertz wave changes with a motion of the flat plate 120. In this way, it is possible to achieve the beam deflection of an incidence terahertz wave. This beam deflection returns to the original position every reciprocating motion end, and is repeated.

In this example, since a linear reciprocating motion instead of rotation is adopted, there is an advantage that it is not necessary to perform correction and suppression of vibration by eccentricity, face tilt, and the like. Nevertheless, it can be said that this correction is almost unnecessary in a terahertz wave which has comparatively long wave length, also when rotating like the example.

Also in this example, when rotating the flat plate 120 around a rotation axis passing through the radiation part 122 with the reciprocating motion, it is possible to deflect an electromagnetic wave two-dimensionally. In this case, for example, a support member which supports the flat plate 120 reciprocably and is equipped with a drive unit for a reciprocating motion is supported by a fixed board rotatably around a rotation axis which coincides with an axis passing through the radiation part 122. In addition, similarly to Example 4, a plurality of grooves 121 may be formed in the flat plate 120 so that intervals of the grooves 121 may changes non-uniformly and regularly according to a formula expressing an interval of an orbicular zone of a Fresnel zone plate in each slender portion extending in a direction approximately orthogonal to the moving direction. Thereby, it is possible to make focal length of a diffracted terahertz wave variable. Furthermore, it is also possible to make the focal length of a diffracted terahertz wave variable with deflecting the diffracted terahertz wave two-dimensionally by combining these constructions.

Example 6

Figure 13:
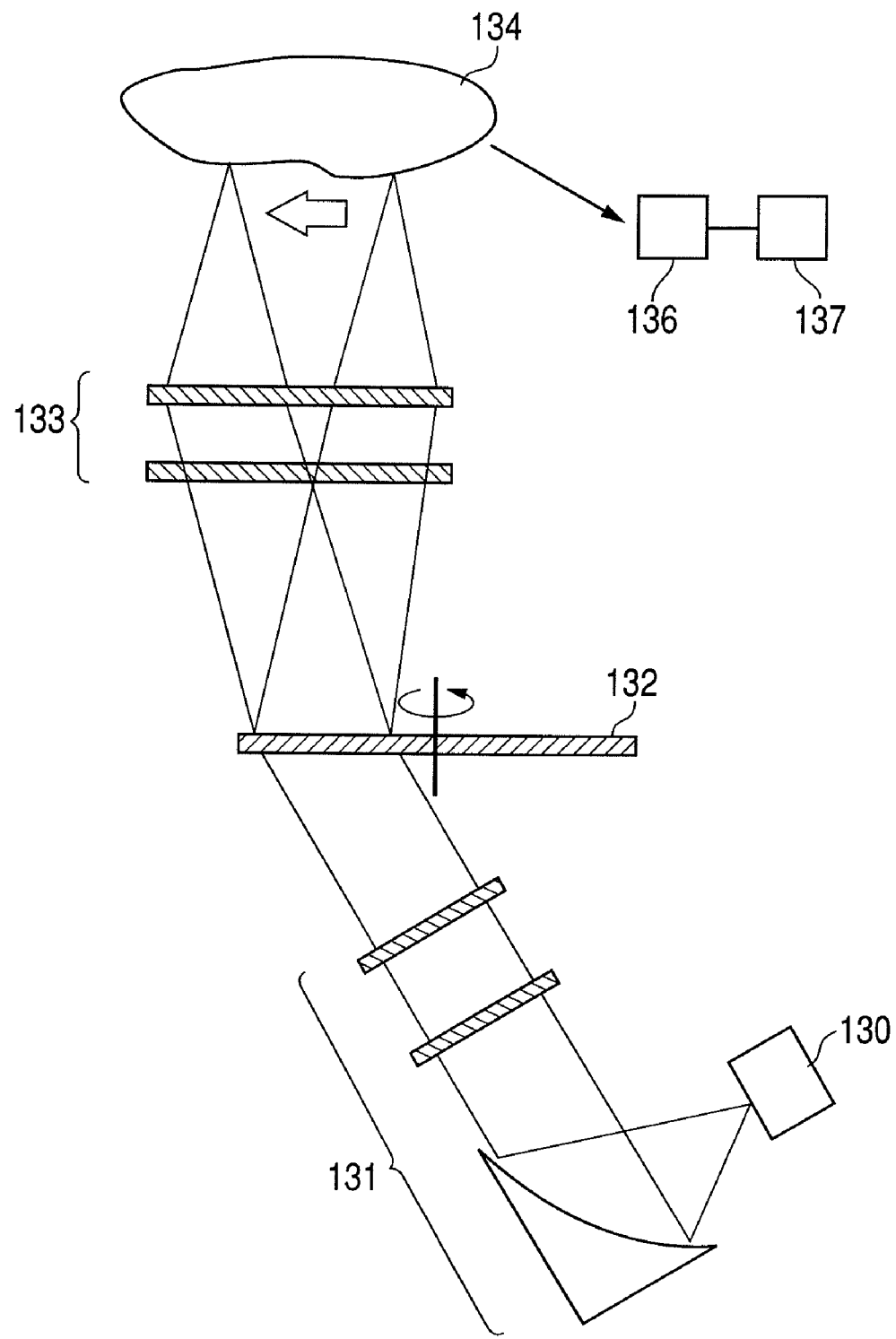
FIG. 13 is a schematic diagram showing an imaging apparatus of Example 6 according to the present invention.

Example 6 of the present invention will be described with referring to FIG. 13. In this example, a terahertz wave generated from a terahertz wave generator 130 is converted into a wave with a suitable beam diameter through an optical system 131, and is incident into a disc-shaped diffraction grating 132 which is described in Example 2. The terahertz wave generator 130 and the optical system 131 construct the electromagnetic wave irradiation unit. The terahertz wave which transmits the disc-shaped diffraction grating 132 is diffracted according to rotation of the disc-shaped diffraction grating 132, and a diffraction angle (that is, deflection angle) changes as illustrated in FIG. 13. Furthermore, the deflected terahertz wave is converged and radiated on an imaging object body 134 through a suitable terahertz wave optical system 133. The optical system 133 includes, for example, a cylindrical lens which has power in a direction perpendicular to a page of FIG. 13, and a Fresnel zone plate which has power in a direction of a plane of FIG. 13.

When the disc-shaped diffraction grating 132 is rotated around a center of the disc, a diffraction angle of the terahertz wave changes and a condensed point of the terahertz wave on the imaging object body 134 moves according to the change. Thereby, terahertz wave imaging can be performed without moving the imaging object body 134.

In addition, when a disc-shaped diffraction grating is used for the optical system 132 as a lens with a variable focal length described in Example 4, even if a position of the imaging object body 134 moves back and forth, it is possible to converge and radiate a wave on the object body 134 with being focused.

Furthermore, the terahertz wave from the imaging object body 134 is detected by a detection unit 136 which is a bolometer, a Schottky barrier diode, or the like. Then, a detection signal from the detection unit 136 is processed in a signal processing unit 137, and an image of the measuring object 134 is obtained. The signal processing unit 137 detects a dielectric constant of each radiation part on the object body 134, and the like from the detection signal, and acquires an image of the measuring object 134 based on these information to make the image displayed in a monitor or the like. By using the deflection device of the present invention, an imaging apparatus of this example can perform beam deflection of even a terahertz wave with a comparatively long wavelength continuously in a comparatively small occupied volume, and can acquire an image of the measuring object 134 favorably.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2007-035572, filed Feb. 16, 2007, which is hereby incorporated by reference herein in its entirety.

What is claimed is:

1. A deflection device, comprising:
  a tabular object for transmitting or reflecting electromagnetic waves;
  a drive unit for driving the tabular object so as to rotate or perform a translation motion; and
  an electromagnetic wave irradiation unit for irradiating the tabular object with electromagnetic wave so that an irradiation area extending in a direction intersecting a direction of the rotation or translation motion of the tabular object is formed, wherein, in order to change a direction of transmission or reflection of electromagnetic wave radiated on the irradiation area by the rotation or translation motion of the tabular object, a plurality of grooves extending in an in-plane direction of the tabular object is provided in a section of the tabular object along a longitudinal direction of the irradiation area, and the plurality of grooves is formed so that intervals of the plurality of grooves which passes through the irradiation area are changed by the rotation or translation motion of the tabular object.

2. The deflection device according to claim 1, wherein the tabular object is rotatable by the drive unit around a rotation axis which passes a rotation center and intersects the plane of the tabular object perpendicularly, and the grooves are formed along a direction of the rotational motion.

3. The deflection device according to claim 1, wherein the tabular object can reciprocate linearly by the drive unit, and the grooves are formed along a direction of the reciprocating motion.

4. The deflection device according to claim 1, wherein the grooves are formed so that intervals of the plurality of grooves in the irradiation area are arranged uniformly, or non-uniformly and regularly.

5. The deflection device according to claim 1, wherein the tabular object is constructed so as to perform not only a rotation or translation motion which the tabular object performs in an in-plane direction, but also a motion in a direction other than the in-plane direction by the drive unit or another drive unit, in order to deflect electromagnetic waves, radiated on the tabular object, two-dimensionally.

6. The deflection device according to claim 1, wherein the plurality of grooves is constructed so that intervals of the plurality of grooves which passes through the irradiation area are changed continuously by the rotation or translation motion of the tabular object.

7. The deflection device according to claim 1, wherein the electromagnetic wave is a terahertz wave.

8. An imaging apparatus, comprising:
  the deflection device according to claim 1;
  a detection unit; and
  a signal processing unit, wherein the detection unit detects an electromagnetic wave, which is reflected or transmitted from a measuring object, with moving an irradiation position of the electromagnetic wave radiated on the measuring object, using the deflection device, and the signal processing unit processes a detection signal from the detection unit to acquire an image of the measuring object.

* * * * *